United States Patent
Sugiyama (10) Patent No.: US 8,121,255 B2
(45) Date of Patent: Feb. 21, 2012

(54) DIAGNOSTIC IMAGING SYSTEM

(75) Inventor: Shinko Sugiyama, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 941 days.

(21) Appl. No.: 12/109,655

(22) Filed: Apr. 25, 2008

(65) Prior Publication Data

US 2009/0034820 A1 Feb. 5, 2009

(30) Foreign Application Priority Data

May 8, 2007 (JP) .................................. 2007-123892

(51) Int. Cl.
*H05G 1/64* (2006.01)
*G21K 4/00* (2006.01)

(52) U.S. Cl. .......................................... 378/98; 378/42
(58) Field of Classification Search .................... 378/42, 378/62, 98, 162, 165, 207; 382/128, 130–132
See application file for complete search history.

(56) References Cited

U.S. PATENT DOCUMENTS

| | | | |
|---|---|---|---|
| 6,577,889 B2 * | 6/2003 | Ichihashi | 600/425 |
| 6,608,884 B1 * | 8/2003 | Mazess et al. | 378/98 |
| 2002/0082498 A1 | 6/2002 | Wendt et al. | 600/411 |

FOREIGN PATENT DOCUMENTS

| | | |
|---|---|---|
| JP | 2004081569 A1 | 3/2004 |
| JP | 2004-538538 | 12/2004 |

OTHER PUBLICATIONS

Office Action dated Dec. 16, 2011, issued by JPO in counterpart Japanese patent application 2007-123892, with translation.

* cited by examiner

*Primary Examiner* — Irakli Kiknadze
(74) *Attorney, Agent, or Firm* — Fitzpatrick, Cella, Harper & Scinto (57) ABSTRACT

A diagnostic imaging system includes a generation unit which generates a fluoroscopic image of X-rays that irradiate a subject, a setting unit which, when displaying the fluoroscopic image superimposed on a field image of a head mounted display, sets the display ratio of the field image and the fluoroscopic image in accordance with a display condition, an image composition unit which generates a composite image by superimposing the fluoroscopic image on the field image on the basis of the ratio set by the setting unit, and an image display unit which displays the composite image on the display unit of the head mounted display.

3 Claims, 10 Drawing Sheets

DIAGNOSTIC IMAGING SYSTEM

BACKGROUND OF THE INVENTION

1. Field of the Invention

The present invention relates to a medical diagnostic imaging technique.

2. Description of the Related Art

Recently, virtual reality technologies have been introduced in the medical field. For the surgical field, operation simulation has been developed, in which surgeons conduct a virtual operation on a trial basis, assuming various techniques and approaches based on the condition of a patient in a preoperative plan. In, for example, conducting endoscopic surgery or using an angiographic imaging apparatus which senses an X-ray fluoroscopic images of the blood flow in blood vessels in which a contrast medium has been injected and allows a doctor to observe and diagnose the image, as in Japanese Patent Laid-Open No. 2004-81569, an operator wearing a head mounted display conducts an operation or makes a diagnosis while observing both a catheter insertion portion and a fluoroscopic image. The above-described system using a virtual reality technology or a head mounted display is sufficiently effective for operation simulation that also serves as a practice or for training of new-fledged doctors.

In a real operation, test, or diagnosis, the operator must be able to instantaneously observe the state or operative field of a patient when his/her condition has taken a sudden turn for the worse, or any trouble has occurred. That is, primary importance to the system is safety in an actual scene more than operability and convenience.

However, if the patient's condition has taken a sharp turn for the worse, or trouble has occurred during diagnosis, the fluoroscopic image displayed on the head mounted display is obstructive.

SUMMARY OF THE INVENTION

The present invention has been made in consideration of the above-described problem, and has as its object to provide a diagnostic imaging technique which ensures safety by setting the ratio of a fluoroscopic image and a field image that is a background image in accordance with a display condition and displaying a composite image of the field image and the fluoroscopic image while changing the display priority order in accordance with the display condition.

According to one aspect of the present invention, there is provided a display control apparatus for controlling display of a radiograph to be displayed on a head mounted display, comprising:

a generation unit adapted to generate an X-ray moving image by detecting X-rays that irradiate a subject;

a setting unit adapted to, when displaying the X-ray moving image superimposed on a main image to be displayed on a display unit of the head mounted display, set a display ratio of the main image and the X-ray moving image in accordance with a display condition;

an image composition unit adapted to generate a composite image by superimposing the X-ray moving image on the main image on the basis of the ratio set by the setting unit;

a display processing unit adapted to display the composite image on the display unit of the head mounted display; and a viewpoint detection unit adapted to detect information about a viewpoint of a user who is wearing the head mounted display, wherein when the viewpoint detection unit detects that the viewpoint of the user exists in a display area of the X-ray moving image, the setting unit switches the ratio to display the X-ray moving image with a priority over the main image, and the image composition unit generates the composite image by superimposing the X-ray moving image on the main image on the basis of the ratio switched by the setting unit.

According to the present invention, it is possible to provide a diagnostic imaging technique which ensures safety by setting the ratio of a fluoroscopic image and a field image.

Further features of the present invention will become apparent from the following description of exemplary embodiments (with reference to the attached drawings).

DESCRIPTION OF THE EMBODIMENTS

A preferred embodiment of the present invention will now be described in detail with reference to the accompanying drawings. The constituent elements described in the embodiment are merely examples. The technical scope of the present invention is defined by the scope of claims and is not limited by the following embodiment.

(Arrangement of X-Ray Diagnostic Imaging System)

Figure 1:
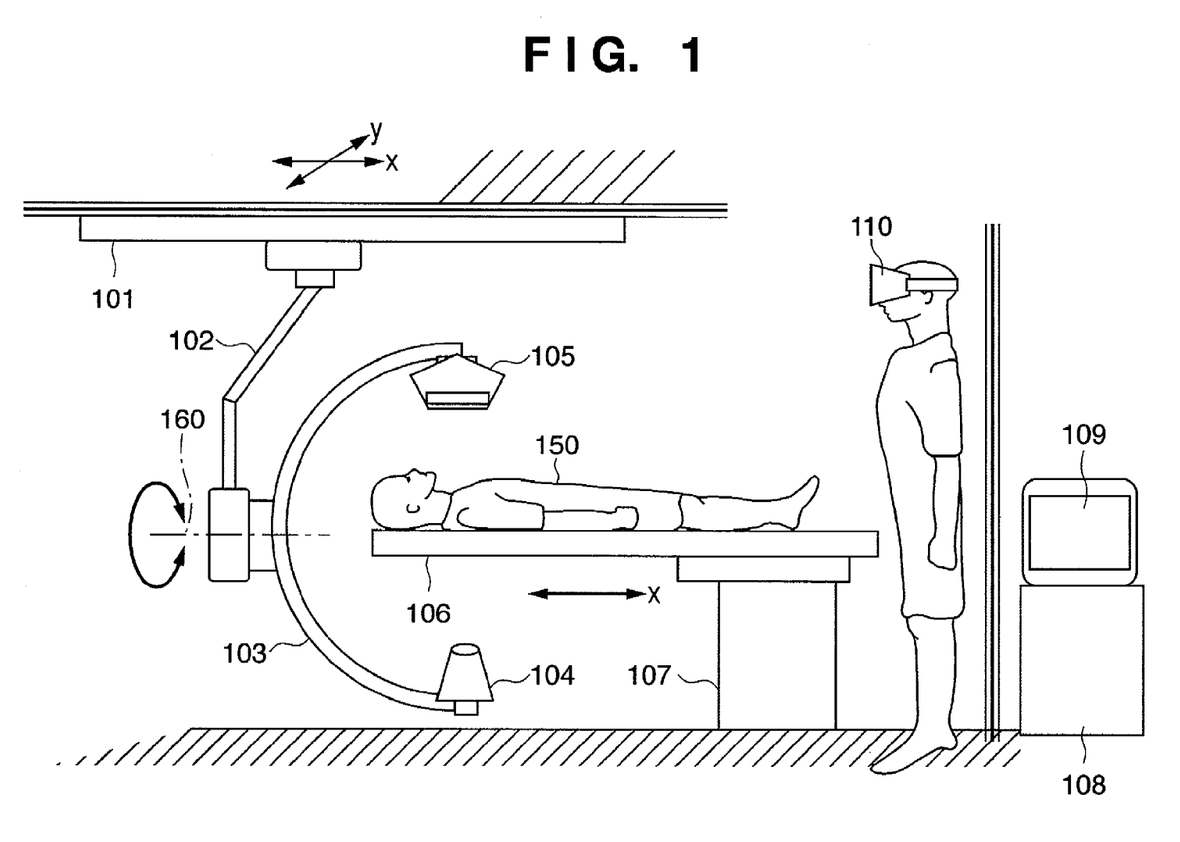
FIG. 1 is a view for explaining the arrangement of a diagnostic imaging system.

FIG. 1 is a view for explaining the arrangement of an X-ray diagnostic imaging system (to be referred to as a diagnostic imaging system hereinafter). The diagnostic imaging system has a C arm 103 that hangs from a ceiling hanging unit 102. The ceiling hanging unit 102 hangs from the ceiling via a moving mechanism 101. The moving mechanism 101 can move in a plane (X- and Y directions) and position the ceiling hanging unit 102. The X-ray diagnostic imaging system functions as a radiograph display control system.

The C arm 103 has, at its lower end, an X-ray tube 104 for irradiating a subject with X-rays. The C arm 103 has, as its upper end, an X-ray receiving unit 105 which receives a radiograph based on the X-rays emitted from the X-ray tube 104. The C arm 103 can rotate about a rotation axis 160 of the ceiling hanging unit 102.

A subject 150 can be placed on a top 106. An examination table 107 can move the top 106 in the X direction.

A head mounted display (to be referred to as an HMD hereinafter) 110 is a medical display control device the operator wears on the head. It is a see-through type HMD capable of observing both a radiographed moving image (fluoroscopic image) and the actual state of a patient. The see-through HMD 110 is usable in the technical field of virtual reality. The HMD 110 looks like a helmet or swimming goggles and is put on the head of an operator or the like. The HMD 110 includes an image input unit which inputs an image, an image display unit which displays an image, a viewpoint detection unit which detects the operator's viewpoint position, and a direction detection unit which detects the tilt of the operator's head.

A display device 109 can display a sensed radiograph.

A control unit 108 can control the overall diagnostic imaging system.

(Internal Arrangement of HMD 110)

There are an HMD of optical see-through type and an HMD of video see-through type.

In the optical see-through type, external light directly reaches the eyes of the HMD wearer. Since a processed image is also displayed simultaneously, the HMD wearer sees the images as if they were superimposed on each other.

Figure 3:
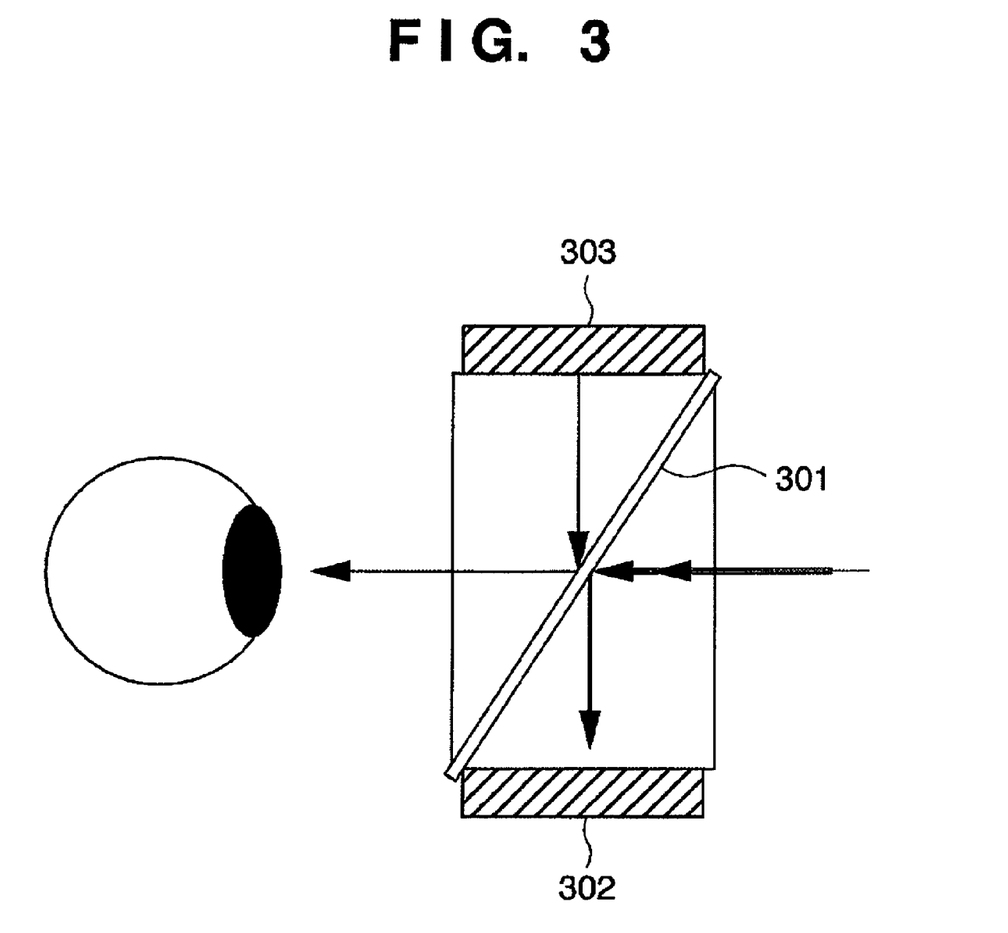
FIG. 3 is a view showing the internal arrangement of a HMD of video see-through type.

In the video see-through type, external light does not directly reach the eyes of the wearer. For example, as shown in FIG. 3, a double-sided mirror 301 changes the direction of external light so that the light strikes an image sensor 302. An image to be presented to the HMD wearer is displayed on a display element 303 and visually recognized by him/her via the double-sided mirror 301. When an external image incident on the image sensor 302 is output to the display element 303, the HMD 110 functions as simple eyeglasses. The HMD 110 can display a processed diagnostic image superimposed on an external image on the display element 303.

The HMD 110 according to this embodiment is preferably of a video see-through type which can receive an image actually seen by the wearer (operator) of the HMD 110 from the image sensor 302. The image received from the image sensor 302 is composited with a fluoroscopic image obtained by X-ray imaging using a method called alpha blending. Then, the composite image can be displayed the display element 303.

(Functional Arrangement of Diagnostic Imaging System)

Figure 11:
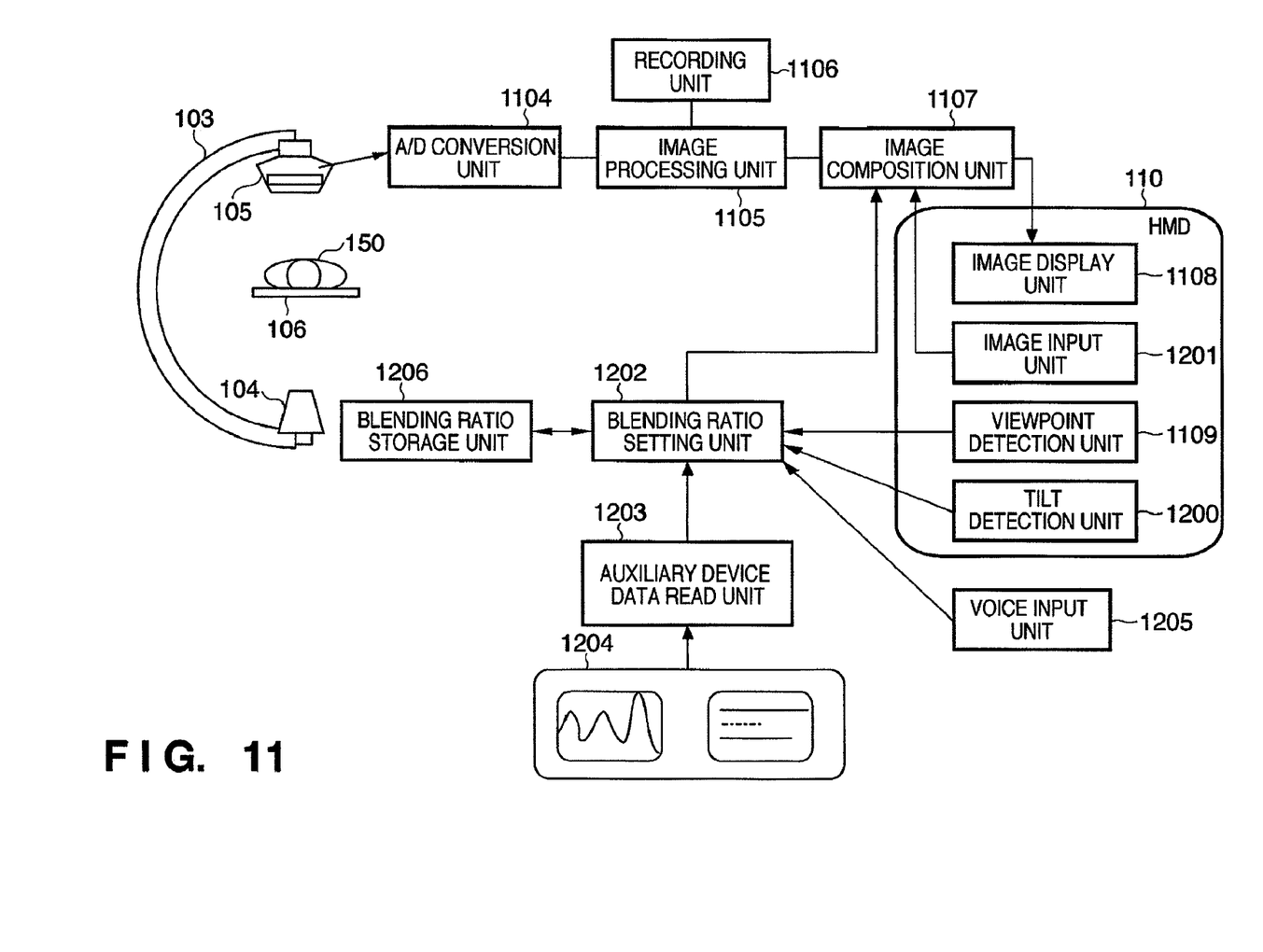
FIG. 11 is a block diagram for explaining the functional arrangement of the diagnostic imaging system.

The functional arrangement of the diagnostic imaging system will be described next with reference to FIG. 11. The same reference numerals as in the diagnostic imaging system shown in FIG. 1 denote the same constituent elements in FIG. 11. The X-ray tube 104 irradiates the subject 150 lying on the top 106 with X-rays. The X-ray receiving unit 105 receives the X-rays transmitted through the subject 150. An amplifier circuit (not shown) converts the X-rays (transmitted X-rays) transmitted through the subject 150 into an optical image. A TV camera converts the optical image into an analog signal.

An A/D conversion unit 1104 converts the analog signal into a digital signal and transmits it to an image processing unit 1105. The image processing unit 1105 executes image processing such as contract and gamma characteristic conversion for the digital image signal received from the A/D conversion unit 1104 and stores the image processing result in a recording unit 1106 formed from, for example, a hard disk.

The X-ray tube 104, X-ray receiving unit 105, A/D conversion unit 1104, and image processing unit 1105 can function as a generation unit which generates a fluoroscopic image of X-rays that have irradiated the subject 150. The image processing unit 1105 transmits the processed fluoroscopic image to an image composition unit 1107.

The HMD 110 includes an image input unit 1201 which inputs a field image, an image display unit 1108 which displays a composite image generated by the image composition unit 1107, a viewpoint detection unit 1109 which detects the operator's viewpoint position, and a tilt detection unit 1200 which detects the tilt of the operator's head.

The viewpoint detection unit 1109 can detect a point on a displayed image, which the operator (wearer) wearing the HMD 110 is looking at.

The viewpoint detection unit 1109 can function as a determination unit which detects information concerning the viewpoint position and viewpoint movement of the head mounted display and determines, based on the detection result, whether to change the display condition.

The tilt detection unit 1200 can detect the tilt of the head of the operator (wearer) who is wearing the HMD 110 by using, for example, a gyro sensor.

The tilt detection unit 1200 can function as a determination unit which detects the tilt of the head mounted display and determines, based on the detection result, whether to change the display condition.

The determination result based on the operator's viewpoint position detected by the viewpoint detection unit 1109 and the determination result based on the tilt of the operator's head detected by the tilt detection unit 1200 are input to a blending ratio setting unit 1202 to be described later.

The image input unit 1201 receives an external field image that the wearer is actually seeing via the HMD 110 and transmits the received field image to the image composition unit 1107 to display a fluoroscopic image superimposed on the field image.

An auxiliary device data read unit 1203 can read medical measurement data (to be referred to as measurement data hereinafter) 1204 of an auxiliary device used for diagnosis and operation. The auxiliary device data read unit 1203 has a function of receiving measurement data of, for example, a sphygmomanometer, electrocardiograph, or contrast medium injector.

The auxiliary device data read unit 1203 can function as a determination unit which analyzes whether the measurement data 1204 falls within a normal range with respect to a reference value and determines, based on the analysis result, whether to change the display condition. The determination result based on the measurement data 1204 read by the auxiliary device data read unit 1203 is sent to the blending ratio setting unit 1202.

A voice input unit 1205 can input (voice-input) the voice of the operator who is wearing the HMD 110 as voice information. The voice input unit 1205 can function as a determination unit which determines, based on comparison between voice input and reference voice information, whether to change the display condition. The determination result by the voice input unit 1205 is sent to the blending ratio setting unit 1202. A word to be used as a key and a voice level reference value are registered in the voice input unit 1205 in advance. The voice input unit 1205 determines whether a voice-input word matches the registered word, or whether the voice level of the input voice exceeds the reference value. The voice input unit 1205 can determine based on this determination whether to change the display condition. The voice input unit 1205 is separated from the HMD 110 in the functional arrangement shown in FIG. 1. However, the HMD 110 may include the voice input unit 1205.

When displaying a fluoroscopic image superimposed on a field image of the head mounted display, the blending ratio setting unit 1202 sets the display ratio of the field image and the fluoroscopic image in accordance with the display condition. This ratio is called a blending ratio. The blending ratio setting unit 1202 sets the blending ratio on the basis of the determination results from the viewpoint detection unit 1109, tilt detection unit 1200, auxiliary device data read unit 1203, and voice input unit 1205 to display the field image and the fluoroscopic image in a different display priority order. In this embodiment, a fluoroscopic image is superimposed on a field image that is the main image. However, a measurement screen of an auxiliary device may be displayed as the main image.

A blending ratio storage unit 1206 can store a plurality of blending ratio settings corresponding to display conditions. The blending ratio storage unit 1206 stores various kinds of information corresponding to display conditions, including a fluoroscopic image blending ratio in an initial display or normal mode, and a display ratio in an emergency mode. The blending ratio setting unit 1202 can refer to the information in the blending ratio storage unit 1206, read out a blending ratio corresponding to a display condition, and set it in the image composition unit 1107.

The image composition unit 1107 can generate a composite image by superimposing an X-ray fluoroscopic image on a field image received by the image input unit 1201 based on the blending ratio set by the blending ratio setting unit 1202.

The image composition unit 1107 inputs the generated composite image to the image display unit 1108 of the HMD 110. Upon receiving the composite image from the image composition unit 1107, the HMD 110 displays it on the image display unit 1108.

(Process of Diagnostic Imaging System Based on Viewpoint Detection)

Figure 2:
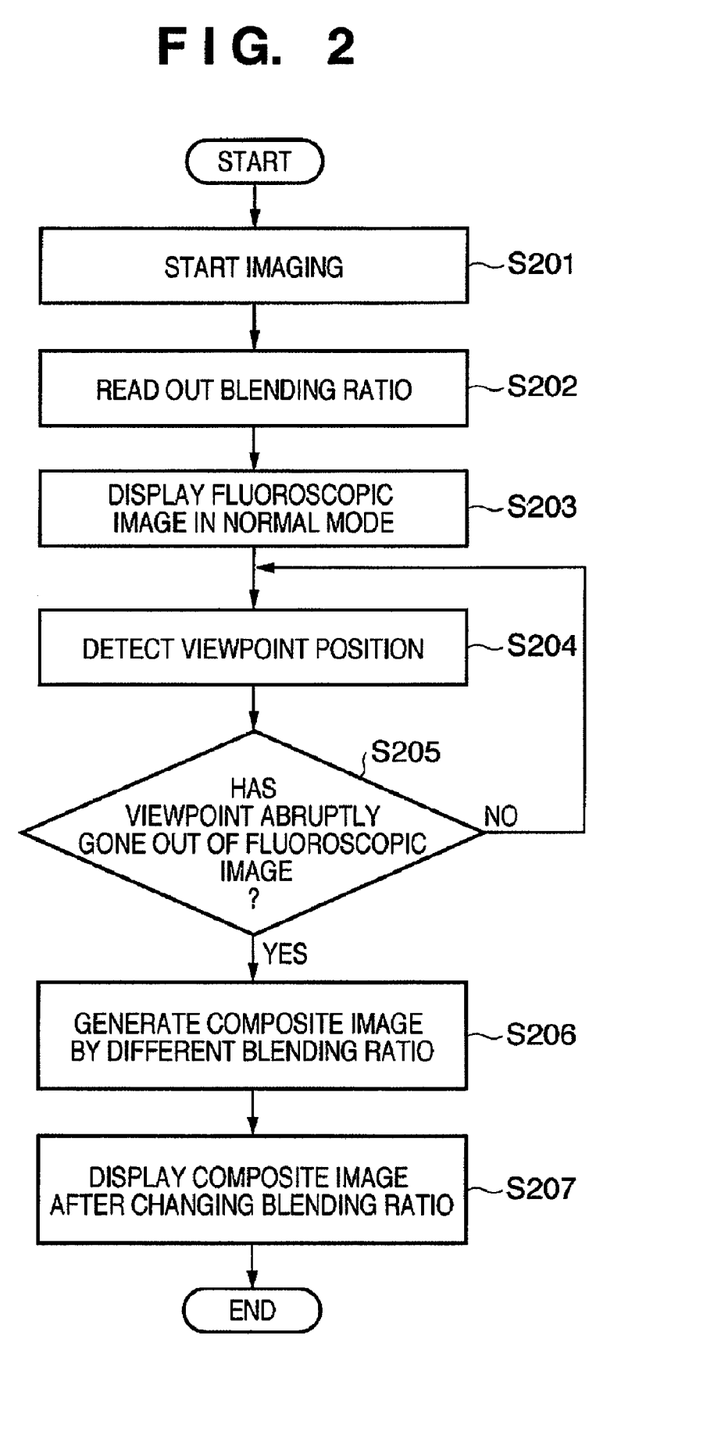
FIG. 2 is a flowchart for explaining the sequence of the process of the diagnostic imaging system based on viewpoint detection.

The sequence of the process of the diagnostic imaging system based on viewpoint detection will be described next with reference to the flowchart in FIG. 2. The blending ratio setting unit 1202 can set a blending ratio based on the operator's viewpoint position, movement (tilt) of the operator's head, voice input information, and the measurement data 1204 read by the auxiliary device data read unit 1203. In the process shown in FIG. 2, the blending ratio setting unit 1202 sets a blending ratio in the image composition unit 1107 based on the information of operator's viewpoint position detected by the viewpoint detection unit 1109. The image composition unit 1107, viewpoint detection unit 1109, and blending ratio setting unit 1202 execute the process in FIG. 2 under the overall control of the control unit 108 of the diagnostic imaging system. First, to prepare for X-ray irradiation, the control unit 108 adjusts the positions of the C arm 103 and the top 106 and aligns the subject 150 as a diagnosis target.

In step S201, X-ray irradiation and imaging start. The X-ray tube 104 starts emitting X-rays. The X-ray receiving unit 105 receives the X-rays transmitted through the subject 150. When the X-ray receiving unit 105 receives the X-rays (transmitted X-rays) transmitted through the subject 150, the amplifier circuit (not shown) described with reference to FIG. 11 converts the transmitted X-rays into an optical image. The TV camera converts the optical image into an analog signal. The A/D conversion unit 1104 converts the analog signal into a digital signal. The image processing unit 1105 executes image processing for the digital signal. A processed fluoroscopic image is input to the image composition unit 1107.

In step S202, the blending ratio setting unit 1202 reads out blending ratios stored in the blending ratio storage unit 1206 in advance. For example, the blending ratio setting unit 1202 sets a fluoroscopic image blending ratio $\alpha 1$ in the initial display or normal mode and a display ratio $\alpha 2$ in the emergency mode to $\alpha 1 = A1$, and $\alpha 2 = A2$ ($0 \leq A1 \leq 1$, $0 \leq A2 \leq 1$). The blending ratio setting unit 1202 inputs the set blending ratios to the image composition unit 1107.

The blending ratio setting unit 1202 can set the blending ratios in the image composition unit 1107 based on information transmitted from the viewpoint detection unit 1109, tilt detection unit 1200, voice input unit 1205, and auxiliary device data read unit 1203.

In step S203, the image input unit 1201 receives an external image (field image) actually seen by the operator and inputs the field image to the image composition unit 1107 as a background image. The image composition unit 1107 can display a moving image of, for example, an operative field or catheter insertion portion as the background image (field image). The image composition unit 1107 generates a composite image by compositing (superimposing) the fluoroscopic image obtained by X-ray imaging with the background image (field image) at the blending ratio ($=\alpha 1$) in the normal mode, which is read out in step S202. The image display unit 1108 displays the composite image in a superimposed manner. To display the superimposed images, a method called alpha blending is usable.

The pixel output format of the image composition unit 1107 contains an opacity A (alpha value) ($0 \leq A \leq 1$) in addition to three primary colors RGBA. The image composition unit 1107 can control generation of the composite image of the background image (field image) and the X-ray fluoroscopic image in accordance with the value of the opacity A. Assume that the RGB values of a pixel of the background image (field image) are (R1,G1,B1), the RGB values of a pixel of the fluoroscopic image are (R2,G2,B2), and the opacity value is A. In this case, the RGB values of the composite image are given by $$(R1 \times (1-A) + R2 \times A, G1 \times (1-A) + G2 \times A, B1 \times (1-A) + B2 \times A) \qquad (1)$$

Hence, when the images are composited using the blending ratio ($A=\alpha 1$) in the normal mode, Expression (1) is rewritten to $$(R1 \times (1-\alpha 1) + R2 \times \alpha 1, G1 \times (1-\alpha 1) + G2 \times \alpha 1, B1 \times (1-\alpha 1) + B2 \times \alpha 1) \qquad (2)$$

Figure 7:
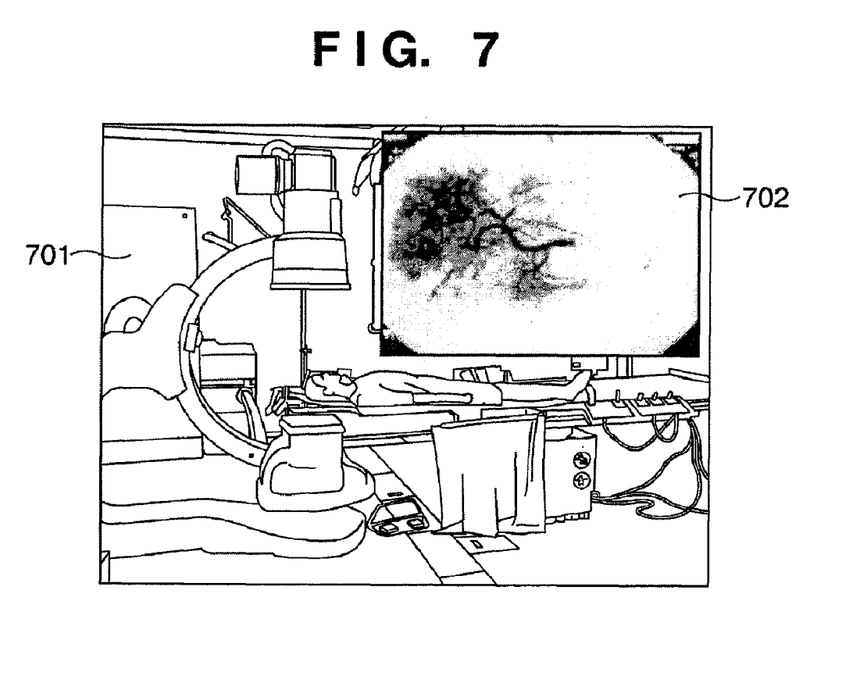
FIG. 7 is a view showing an example of display of a fluoroscopic image and a background image.

When the blending ratio $\alpha 1 = 1$, the RGB values of the composite image equal the RGB values (R2,G2,B2) of the fluoroscopic image. The operator cannot see the background image (field image) through the fluoroscopic image at all. FIG. 7 is a view showing an example of display of a fluoroscopic image and a background image (field image). When a background image 701 and a fluoroscopic image 702 are composited using the blending ratio $\alpha 1 = 1$, the fluoroscopic image 702 is displayed on the near side, and the background image 701 is invisible. The image display unit 1108 of the HMD 110 displays the image composited by the image composition unit 1107.

In step S204, the viewpoint detection unit 1109 detects the operator's viewpoint position.

In step S205, the viewpoint detection unit 1109 determines, based on the detection result of the operator's viewpoint position, whether the operator's viewpoint has gone out of the area of the X-ray fluoroscopic image. If the operator's viewpoint exists in the area of the X-ray fluoroscopic image (e.g., within the range of the fluoroscopic image 702 in FIG. 7) without going out of the area (NO in step S205), the process returns to step S204 to cause the viewpoint detection unit 1109 to repeatedly detect the operator's viewpoint position.

If it is determined in step S205 that the operator's viewpoint has gone out of the area of the fluoroscopic image, and the time required for the viewpoint movement is shorter than a predetermined reference time (YES in step S205), the process advances to step S206. The viewpoint detection unit 1109 can measure the coordinates of the operator's viewpoint position and the viewpoint measurement time. The viewpoint detection unit 1109 can use a timer (not shown) to measure the measurement time.

Figure 8:
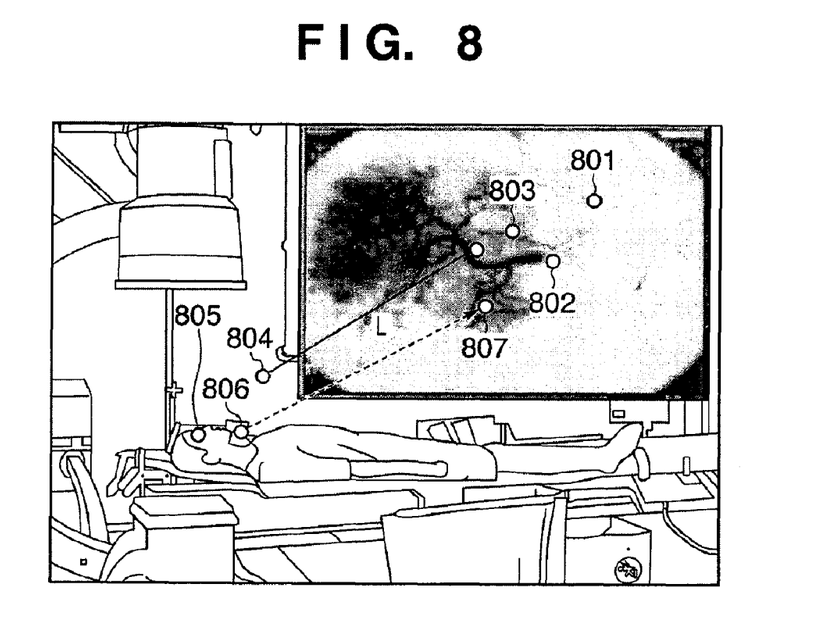
FIG. 8 is a view for explaining movement of an operator's viewpoint.

FIG. 8 is a view for explaining movement of the operator's viewpoint. The viewpoint detection unit 1109 can periodically detect the position of the viewpoint of the operator who is wearing the HMD 110. In FIG. 8, viewpoints 801, 802, . . . , and 807 indicate viewpoint positions detected by the viewpoint detection unit 1109. The position coordinates of the respective viewpoints are represented by the viewpoint 801 (X1,Y1), viewpoint 802 (X2,Y2), . . . , and viewpoint 807 (X7,Y7). The viewpoint detection times are represented by t1, t2, . . . , and t7. The viewpoint detection unit 1109 determines the times t1, t2, t3, . . . , and t7 by referring to the timer upon detecting the position coordinates. The time elapses in the order of t1→t2→t3→ . . . →t7. Referring to FIG. 8, the viewpoint 804 (X4,Y4) is detected outside the area of the fluoroscopic image 702. The viewpoint 807 (X7,Y7) is measured when the viewpoint has returned inside the area of the fluoroscopic image 702.

Examine the viewpoints 803 and 804. The viewpoint detection unit 1109 calculates the moving time (t4−t3) from the viewpoint 803 in the area of the fluoroscopic image 702 to the viewpoint 804 outside the area of the fluoroscopic image 702 and compares the time with the reference time. If the viewpoint detection unit 1109 determines in step S205 that the moving time (t4−t3) is shorter than the reference time (YES in step S205), the process advances to step S206.

On the other hand, if the viewpoint detection unit 1109 determines that the moving time (t4−t3) is longer than the reference time (NO in step S205), the process returns to step S204 to cause the viewpoint detection unit 1109 to repeatedly detect the viewpoint position. The viewpoint detection unit 1109 determines whether each detected viewpoint exists within the fluoroscopic image area. When the viewpoint has gone out of the fluoroscopic image area, the viewpoint detection unit 1109 compares the moving time with the reference time. When the moving time is shorter than the reference time, the viewpoint detection unit 1109 determines emergency and inputs identification information representing the emergency to the blending ratio setting unit 1202.

The blending ratio setting unit 1202 can switch the blending ratio setting based on the identification information received from the viewpoint detection unit 1109. The blending ratio setting unit 1202 switches the blending ratio $\alpha 1$ set for the fluoroscopic image in the initial display or normal mode to the blending ratio $\alpha 2$ in the emergency mode and sets it in the image composition unit 1107.

In step S206, the image composition unit 1107 receives the setting of the blending ratio $\alpha 2$ in the emergency mode and composites the fluoroscopic image with the background image (field image) based on the set blending ratio $\alpha 2$ in the emergency mode. The images are composited using the above-described alpha blending method. When the RGB values of a pixel of the background image (field image) are represented by (R1,G1,B1), the RGB values of a pixel of the fluoroscopic image are represented by (R2,G2,B2), and the blending ratio in the emergency mode is represented by $\alpha 2$, the RGB values of the composite image are given by $$(R1\times(1-\alpha 2)+R2\times\alpha 2, G1\times(1-\alpha 2)+G2\times\alpha 2, B1\times(1-\alpha 2)+B2\times\alpha 2) \quad (3)$$

In step S207, the image display unit 1108 of the HMD 110 displays the composite image generated by the image composition unit 1107 in step S206.

Upon detecting an operator's steady gaze on the fluoroscopic image or the background image (field image) for a predetermined time, the viewpoint detection unit 1109 can determine that the state has returned from the emergency mode to the normal mode. The viewpoint detection unit 1109 inputs, to the blending ratio setting unit 1202, identification information representing that the state has returned to the normal mode. The blending ratio setting unit 1202 switches the blending ratio $\alpha 2$ in the emergency mode to the blending ratio $\alpha 1$ in the normal mode and sets it in the image composition unit 1107 to change the image display in the emergency mode to that in the normal mode.

Figure 9:
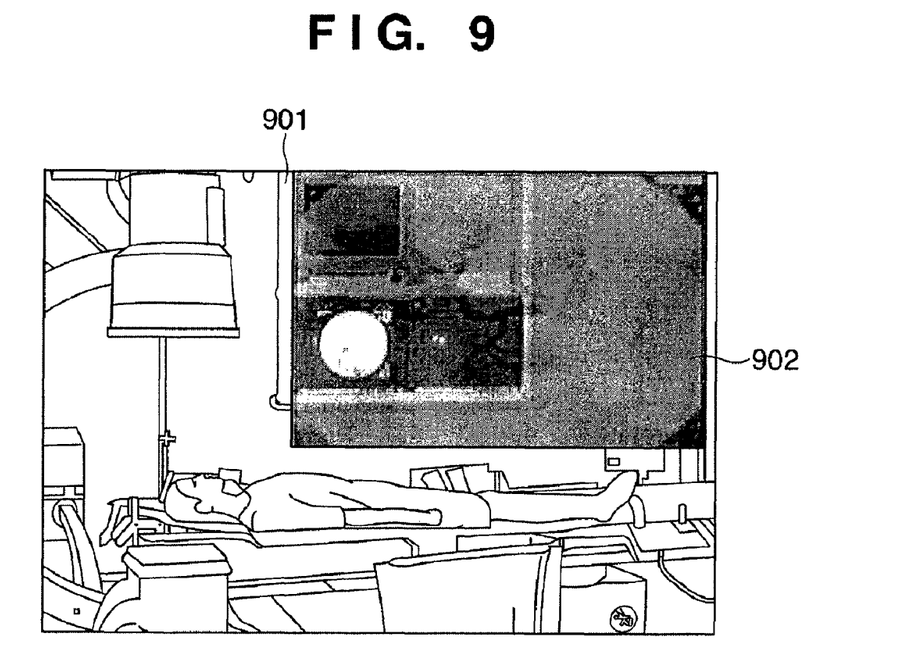
FIG. 9 is a view showing an image displayed on an HMD 110 in case of emergency.

FIG. 9 is a view showing an example of an image displayed on the HMD 110 in case of emergency. The operator can see a background image 901 including the state of the patient and the monitors of apparatuses through a fluoroscopic image 902. This allows the operator to more accurately confirm the situation without taking off the HMD 110.

(Process of Diagnostic Imaging System Based on Head Tilt Detection Amount)

Figure 4:
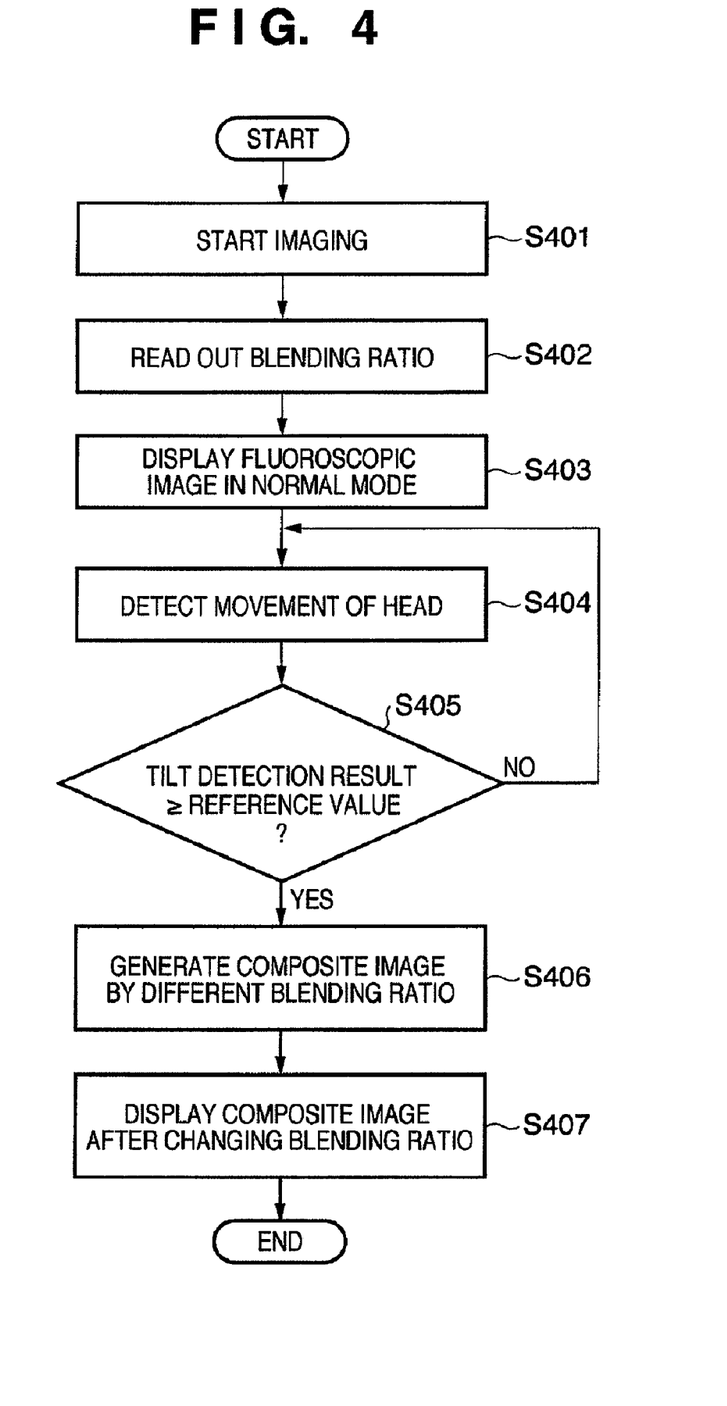
FIG. 4 is a flowchart for explaining the sequence of the process of the diagnostic imaging system based on head tilt detection.

The sequence of the process of the diagnostic imaging system based on detection of the movement (tilt) of the head of the operator who is wearing the HMD 110 will be described next with reference to the flowchart in FIG. 4. The image composition unit 1107, tilt detection unit 1200, and blending ratio setting unit 1202 execute the process in FIG. 4 under the overall control of the control unit 108 of the diagnostic imaging system. In steps S401 to S403 of FIG. 4, the same process as in steps S201 to S203 of the flowchart in FIG. 2 is executed.

In step S404, the tilt detection unit 1200 detects the movement (tilt) of the head of the operator who is wearing the HMD 110. Using, for example, a gyro sensor as a tilt detection mechanism, the tilt detection unit 1200 can detect the movement (tilt) of the head of the operator who is wearing the HMD 110 as an amount of tilt in an action of, for example, moving the head from side to side or up and down.

In step S405, the tilt detection unit 1200 compares the detection result (tilt amount) of the movement (tilt) of the head of the operator who is wearing the HMD 110 with a predetermined tilt reference value. If the detection result (tilt amount) is equal to or more than the tilt reference value, the tilt detection unit 1200 determines an emergency and inputs identification information representing the emergency to the blending ratio setting unit 1202.

The blending ratio setting unit 1202 can switch the blending ratio setting based on the identification information received from the tilt detection unit 1200. The blending ratio setting unit 1202 switches the blending ratio $\alpha 1$ set for the fluoroscopic image in the initial display or normal mode to the blending ratio $\alpha 2$ in the emergency mode and sets it in the image composition unit 1107.

In step S406, the image composition unit 1107 receives the setting of the blending ratio $\alpha 2$ in the emergency mode and composites the fluoroscopic image with the background image (field image) based on the set blending ratio $\alpha 2$ in the emergency mode. The images can be composited using the above-described alpha blending method. When the RGB values of a pixel of the background image (field image) are represented by (R1,G1,B1), the RGB values of a pixel of the fluoroscopic image are represented by (R2,G2,B2), and the blending ratio in the emergency mode is represented by $\alpha 2$, the RGB values of the composite image are given by Expression (3), as described above.

In step S407, the image display unit 1108 of the HMD 110 displays the composite image generated by the image composition unit 1107 in step S406.

Upon detecting another head tilt (e.g., moving the head back and forth or from side to side) as a trigger, the tilt detection unit 1200 can determine that the state has returned from the emergency mode to the normal mode. The tilt detection unit 1200 inputs, to the blending ratio setting unit 1202, identification information representing that the state has returned to the normal mode. The blending ratio setting unit 1202 switches the blending ratio α2 in the emergency mode to the blending ratio α1 in the normal mode and sets it in the image composition unit 1107 to change the image display in the emergency mode to that in the normal mode.

(Process of Diagnostic Imaging System Based on Voice Input)

Figure 5:
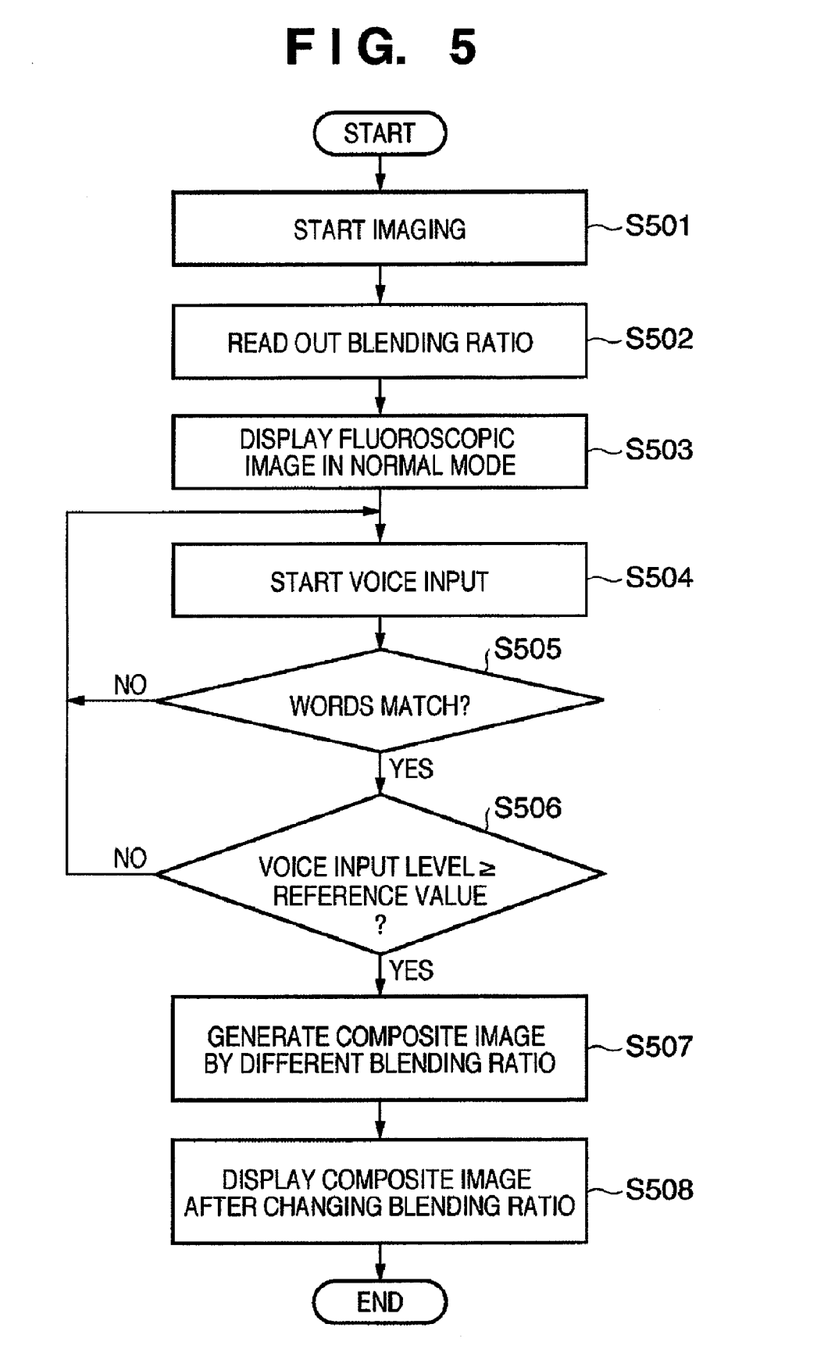
FIG. 5 is a flowchart for explaining the sequence of the process of the diagnostic imaging system based on voice input.

The sequence of the process of the diagnostic imaging system based on voice input will be described next with reference to the flowchart in FIG. 5. The image composition unit 1107, voice input unit 1205, and blending ratio setting unit 1202 execute the process in FIG. 5 under the overall control of the control unit 108 of the diagnostic imaging system. In steps S501 to S503 of FIG. 5, the same process as in steps S201 to S203 of the flowchart in FIG. 2 is executed.

In step S504, the voice input unit 1205 starts a voice input process.

In step S505, the voice input unit 1205 determines whether the voice-input word matches a word that is registered in advance as a key. If the voice input unit 1205 determines that the voice-input word does not match the word registered in advance (NO in step S505), the process returns to step S504.

If the voice input unit 1205 determines in step S505 that the voice-input word matches the word registered in advance (YES in step S505), the process advances to step S506.

In step S506, the voice input unit 1205 compares the voice level of the input word with a predetermined voice level reference value. If the voice level of the input word is equal to or more than the voice level reference value, the voice input unit 1205 determines emergency (YES in step S506). The voice input unit 1205 inputs identification information representing the emergency to the blending ratio setting unit 1202.

If it is determined in step S506 that the voice level of the input word is less than the voice level reference value (NO in step S506), the process returns to step S504 to repeat the voice input process.

The blending ratio setting unit 1202 can switch the blending ratio setting based on the identification information received from the voice input unit 1205. The blending ratio setting unit 1202 switches the blending ratio α1 set for the fluoroscopic image in the initial display or normal mode to the blending ratio α2 in the emergency mode and sets it in the image composition unit 1107.

In step S507, the image composition unit 1107 receives the setting of the blending ratio α2 in the emergency mode and composites the fluoroscopic image with the background image (field image) based on the set blending ratio α2 in the emergency mode. The images can be composited using the above-described alpha blending method. When the RGB values of a pixel of the background image (field image) are represented by (R1,G1,B1), the RGB values of a pixel of the fluoroscopic image are represented by (R2,G2,B2), and the blending ratio in the emergency mode is represented by α2, the RGB values of the composite image are given by Expression (3), as described above.

In step S508, the image display unit 1108 of the HMD 110 displays the composite image generated by the image composition unit 1107 in step S507.

Upon detecting another voice input that satisfies the references (S505 and S506), the voice input unit 1205 can determine that the state has returned from the emergency mode to the normal mode. The voice input unit 1205 inputs, to the blending ratio setting unit 1202, identification information representing that the state has returned to the normal mode. The blending ratio setting unit 1202 switches the blending ratio α2 in the emergency mode to the blending ratio α1 in the normal mode and sets it in the image composition unit 1107 to change the image display in the emergency mode to that in the normal mode.

(Process of Diagnostic Imaging System Based on Measurement Data 1204)

The sequence of the process of the diagnostic imaging system based on the measurement data 1204 read by the auxiliary device data read unit 1203 will be described next with reference to the flowchart in FIG. 6.

Figure 6:
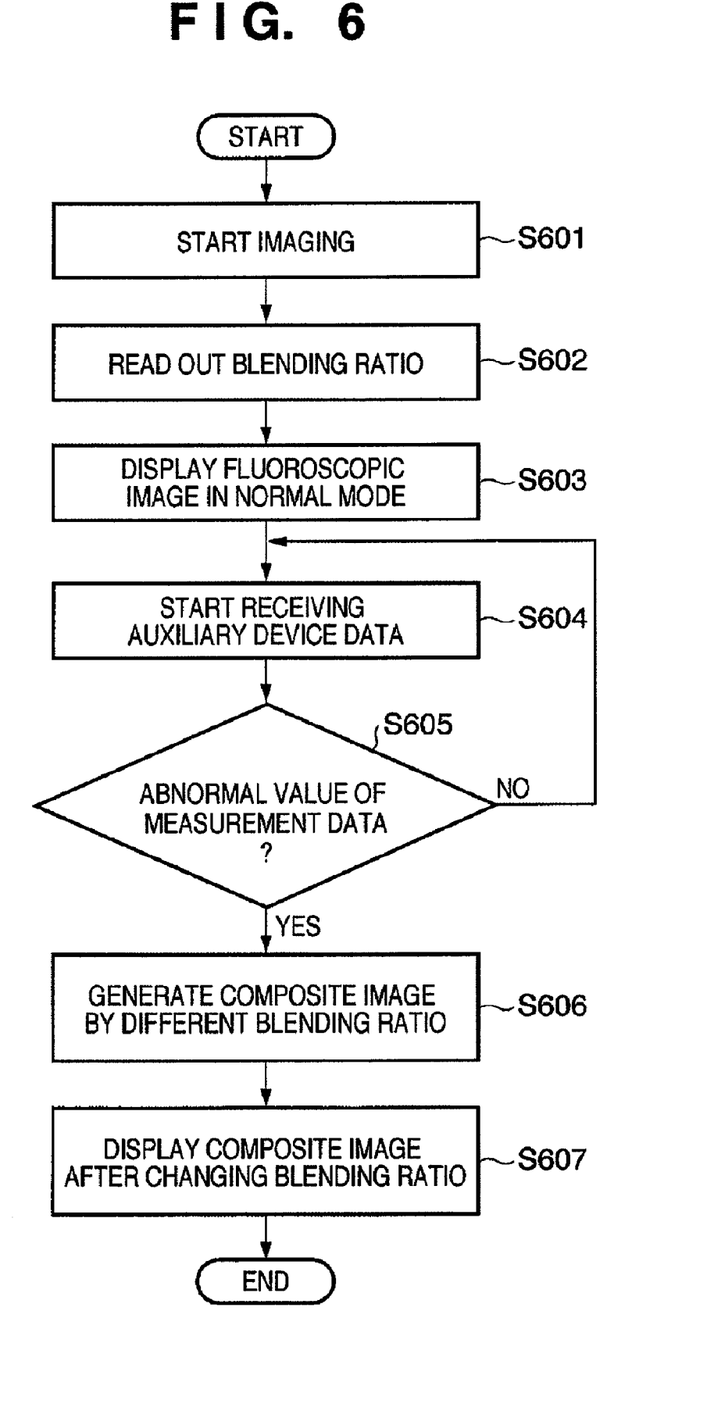
FIG. 6 is a flowchart for explaining the sequence of the process of the diagnostic imaging system based on measurement data of an auxiliary device.

The image composition unit 1107, auxiliary device data read unit 1203, and blending ratio setting unit 1202 execute the process in FIG. 6 under the overall control of the control unit 108 of the diagnostic imaging system. In steps S601 to S603 of FIG. 6, the same process as in steps S201 to S203 of the flowchart in FIG. 2 is executed.

In step S604, the auxiliary device data read unit 1203 starts reading the medical measurement data 1204 associated with the subject 150 from a medical auxiliary device. A medical auxiliary device indicates a medical device necessary for a test, diagnosis, or operation, including an electrocardiograph and a sphygmomanometer.

Figure 10:
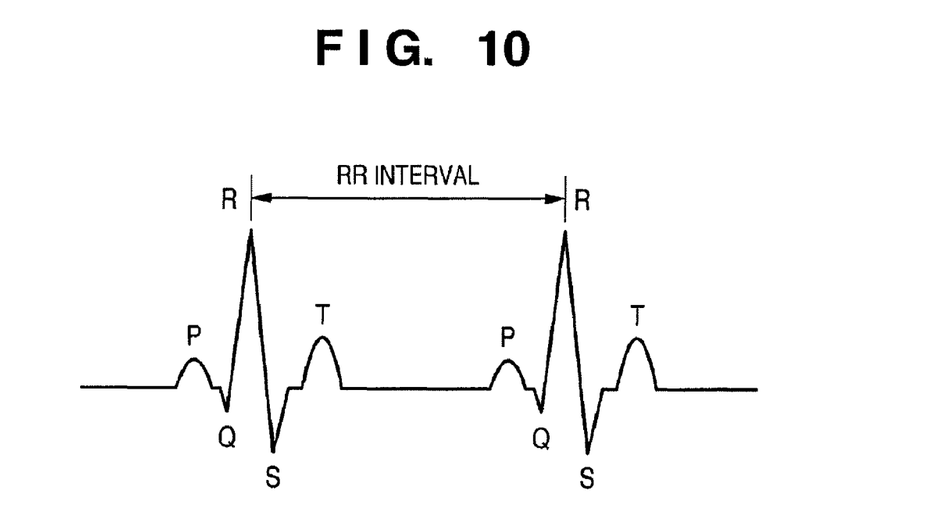
FIG. 10 is a view for explaining measurement data of an electrocardiograph.

FIG. 10 is a view showing an electrocardiographic wave as an example of the measurement data 1204. The P wave in FIG. 10 indicates the atrial activity. The QRS wave indicates the venticular systole. The T wave indicates the process of returning the contracted heart to the initial state. It is possible to estimate an abnormality of the heart by comparing the waveform and rhythm based on the measurement data 1204 with a normal waveform. For example, an irregularity in the RR interval indicates fluctuations in the rhythm of heart beat. The rise and fall of the waveform in the ST interval are key factors mainly in determining an ischemic heart disease.

In step S605, under the control of the control unit 108, the auxiliary device data read unit 1203 compares the measurement data 1204 read from the auxiliary device with a medical data reference value that is set in advance as normal medical data in each auxiliary device. The control unit 108 and the auxiliary device data read unit 1203 can function as an analysis unit which analyzes whether the measurement data 1204 falls within a normal range with respect to the medical data reference value.

Under the control of the control unit 108, if the difference between the read measurement data 1204 and the medical data reference value is equal to or larger than a predetermined value, the auxiliary device data read unit 1203 determines that the measurement data 1204 is abnormal (emergency). The auxiliary device data read unit 1203 inputs identification information representing the emergency to the blending ratio setting unit 1202.

The blending ratio setting unit 1202 can switch the blending ratio setting based on the identification information received from the auxiliary device data read unit 1203. The blending ratio setting unit 1202 switches the blending ratio α1 set for the fluoroscopic image in the initial display or normal mode to the blending ratio α2 in the emergency mode and sets it in the image composition unit 1107.

In step S606, the image composition unit 1107 receives the setting of the blending ratio α2 in the emergency mode and composites the fluoroscopic image with the background image (field image) based on the set blending ratio α2 in the emergency mode. The images can be composited using the above-described alpha blending method. When the RGB values of a pixel of the background image (field image) are represented by (R1,G1,B1), the RGB values of a pixel of the fluoroscopic image are represented by (R2,G2,B2), and the blending ratio in the emergency mode is represented by α2, the RGB values of the composite image are given by Expression (3), as described above.

In step S607, the image display unit 1108 of the HMD 110 displays the composite image generated by the image composition unit 1107 in step S606.

Upon detecting that the difference between the measurement data 1204 and the medical data reference value is smaller than the predetermined value, the auxiliary device data read unit 1203 can determine that the state has returned from the emergency mode to the normal mode. The auxiliary device data read unit 1203 inputs, to the blending ratio setting unit 1202, identification information representing that the state has returned to the normal mode. The blending ratio setting unit 1202 switches the blending ratio α2 in the emergency mode to the blending ratio α1 in the normal mode and sets it in the image composition unit 1107 to change the image display in the emergency mode to that in the normal mode.

In the above description, the blending ratio setting unit 1202 can flexibly set the blending ratio of the diagnostic image and the background image (field image) in the initial display mode in accordance with the application purpose. The blending ratio setting unit 1202 can arbitrarily set the diagnostic image blending ratio within the range of 0.0 to 1.0.

For example, when injecting a contrast medium in a blood vessel using a catheter, and observing and diagnosing the blood flow on the basis of an X-ray fluoroscopic image, the blending ratio setting unit 1202 sets the blending ratio in the initial (normal) mode to α1=1, and the blending ratio in the emergency mode to α2=0.3.

When the blending ratio α1=1, the RGB values of the composite image equal the RGB values (R2,G2,B2) of the fluoroscopic image, as described with reference to Expression (2). The operator cannot see the background image (field image) through the fluoroscopic image at all. When the blending ratio α1=1 is set, the image composition unit 1107 can control the display of the composite image by giving a higher priority to the X-ray fluoroscopic image.

When the blending ratio α2=0.3, the image composition unit 1107 generates a composite image by compositing the background image (field image) with the X-ray fluoroscopic image by a ratio of 7:3. The image composition unit 1107 can also control the display of the composite image by giving a higher priority to the background image (field image) so that the operator can observe the patient state or the field around the hands of his/her own in case of emergency.

On the other hand, for, for example, a heart surgery, the blending ratio setting unit 1202 sets α1=0.3 contrary to a test or the like. It is therefore possible to display the X-ray fluoroscopic image with a priority over the background image (field image) in the initial (normal) mode.

Figure 12:
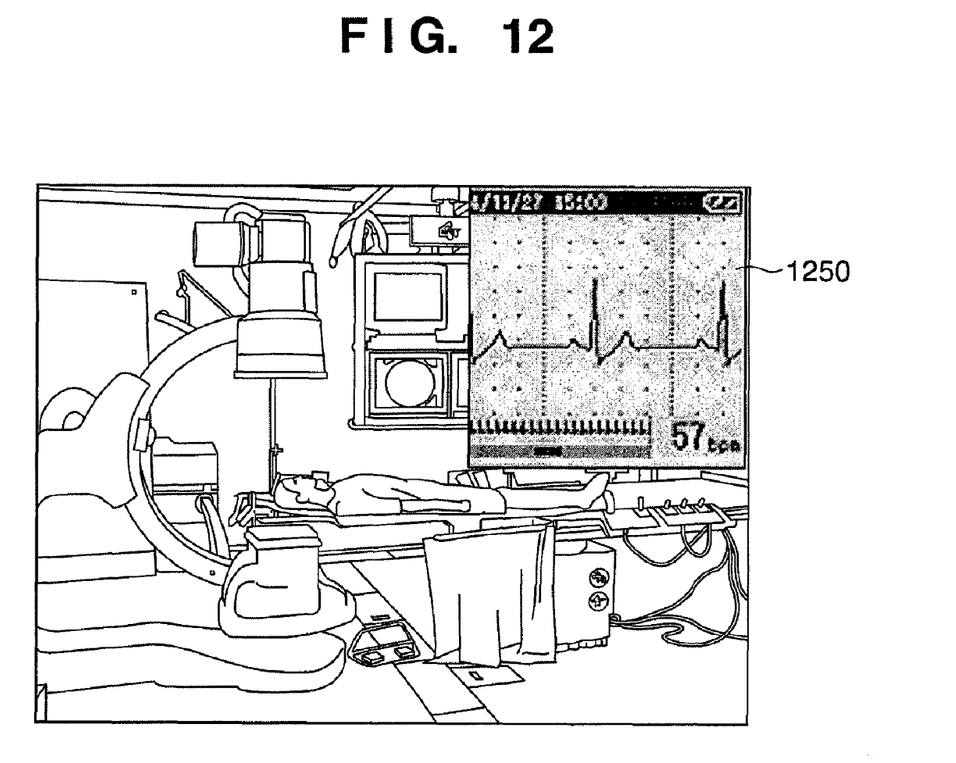
FIG. 12 is a view showing an example in which measurement data of an electrocardiograph is displayed as a diagnostic image.

In the initial (normal) mode, the background image (field image) of, for example, an operative field is easy to see. If an abnormality is detected, the blending ratio setting unit 1202 switches the blending ratio setting. In case of emergency, the blending ratio setting unit 1202 sets α2=1 so that an electrocardiographic indicator 1250 of the measurement data 1204 can be displayed as a diagnostic image, as shown in FIG. 12, to quickly confirm the cause of the abnormality.

It is possible to provide a diagnostic imaging technique which ensures safety by setting the ratio of a fluoroscopic image and a field image that is a background image in accordance with a display condition and displaying a composite image of the field image and the fluoroscopic image while changing the display priority order in accordance with the display condition.

That is, according to the embodiment, it is possible to provide a diagnostic imaging technique which ensures safety by controlling the composition ratio of a field image and a fluoroscopic image to be displayed on a head mounted display.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-123892, filed May 8, 2007, which is hereby incorporated by reference herein in its entirety.

What is claimed is:

1. A display control apparatus for controlling display of a radiograph to be displayed on a head mounted display, comprising:
   a generation unit adapted to generate an X-ray moving image by detecting X-rays that irradiate a subject;
   a setting unit adapted to, when displaying the X-ray moving image superimposed on a main image to be displayed on a display unit of the head mounted display, set a display ratio of the main image and the X-ray moving image in accordance with a display condition;
   an image composition unit adapted to generate a composite image by superimposing the X-ray moving image on the main image on the basis of the ratio set by said setting unit;
   a display processing unit adapted to display the composite image on the display unit of the head mounted display; and
   a viewpoint detection unit adapted to detect information about a viewpoint of a user who is wearing the head mounted display,
   wherein when said viewpoint detection unit detects that the viewpoint of the user exists in a display area of the X-ray moving image, said setting unit switches the ratio to display the X-ray moving image with a priority over the main image, and
   said image composition unit generates the composite image by superimposing the X-ray moving image on the main image on the basis of the ratio switched by said setting unit.

2. A radiographic image display control apparatus comprising:
   a generation unit adapted to generate an X-ray moving image by detecting X-rays that irradiate a subject;
   a setting unit adapted to, when displaying the X-ray moving image superimposed on a main image to be displayed on a head mounted display, set a display ratio of the main image and the X-ray moving image in accordance with a display condition;
   an image composition unit adapted to generate a composite image by superimposing the X-ray moving image on the main image on the basis of the ratio set by said setting unit;
   a display processing unit adapted to display the composite image on a display unit of the head mounted display; and
   a tilt detection unit adapted to detect a tilt of the head mounted display, wherein when said tilt detection unit detects that the tilt of the head mounted display is not less than a reference value, said setting unit switches the ratio to display the X-ray moving image with a priority over the main image, and said image composition unit generates the composite image by superimposing the X-ray moving image on the main image on the basis of the ratio switched by said setting unit.

3. A radiographic image display control apparatus comprising:

a generation unit adapted to generate an X-ray moving image by detecting X-rays that irradiate a subject;

a setting unit adapted to, when displaying the X-ray moving image superimposed on a main image to be displayed on a head mounted display, set a display ratio of the main image and the X-ray moving image in accordance with a display condition;

an image composition unit adapted to generate a composite image by superimposing the X-ray moving image on the main image on the basis of the ratio set by said setting unit;

an image display unit adapted to display the composite image on a display unit of the head mounted display;

a read unit adapted to read measurement data of an auxiliary device; and an analysis unit adapted to analyze whether the measurement data falls within a normal range with respect to a reference value, wherein when said analysis unit analyzes that the measurement data falls outside the normal range with respect to the reference value, said setting unit switches the ratio to display the X-ray moving image with a priority over the main image, and said image composition unit generates the composite image by superimposing the X-ray moving image on the main image on the basis of the ratio switched by said setting unit.

* * * * *